(12) United States Patent
Foerster

(10) Patent No.: US 8,414,599 B1
(45) Date of Patent: Apr. 9, 2013

(54) DYNAMIC SUTURE TENSIONING DEVICE AND METHODS

(75) Inventor: Seth A. Foerster, San Clemente, CA (US)

(73) Assignee: Dallen Medical, Inc., San Clemente, CA (US)

( * ) Notice: Subject to any disclaimer, the term of this patent is extended or adjusted under 35 U.S.C. 154(b) by 939 days.

(21) Appl. No.: 12/347,821

(22) Filed: Dec. 31, 2008

Related U.S. Application Data

(60) Provisional application No. 61/018,116, filed on Dec. 31, 2007.

(51) Int. Cl.
*A61B 17/10* (2006.01)

(52) U.S. Cl. .................................................. 606/139

(58) Field of Classification Search .............. 606/228, 606/232, 233, 139, 144, 145, 74, 103, 104, 606/151, 69, 72, 105
See application file for complete search history.

(56) References Cited

U.S. PATENT DOCUMENTS

| | | | |
|---|---|---|---|
| 303,360 A | 8/1884 | Brunner | |
| 3,822,445 A | 7/1974 | Feng | |
| 4,279,248 A | 7/1981 | Gabbay | |
| 4,444,181 A * | 4/1984 | Wevers et al. | 606/75 |
| 4,535,772 A * | 8/1985 | Sheehan | 606/218 |
| 4,667,675 A * | 5/1987 | Davis | 606/233 |
| 4,730,615 A | 3/1988 | Sutherland et al. | |
| 4,813,416 A | 3/1989 | Pollak et al. | |
| 4,901,721 A | 2/1990 | Hakki | |
| 4,938,760 A | 7/1990 | Burton et al. | |
| 4,959,064 A | 9/1990 | Engelhardt | |
| 4,969,892 A | 11/1990 | Burton et al. | |
| 5,330,489 A | 7/1994 | Green et al. | |
| 5,339,870 A | 8/1994 | Green et al. | |
| 5,366,461 A | 11/1994 | Blasnik | |
| 5,571,105 A | 11/1996 | Gundolf | |
| 5,722,976 A | 3/1998 | Brown | |
| 5,797,915 A | 8/1998 | Pierson, III et al. | |
| 5,807,214 A | 9/1998 | Riazi | |
| 5,810,854 A | 9/1998 | Beach | |
| 5,849,012 A * | 12/1998 | Abboudi | 606/57 |
| 5,972,006 A | 10/1999 | Sciaino, Jr. | |
| 6,051,007 A | 4/2000 | Hogendijk et al. | |
| 6,066,160 A | 5/2000 | Colvin et al. | |
| 6,080,185 A | 6/2000 | Johnson et al. | |
| 6,471,715 B1 | 10/2002 | Weiss | |
| 6,540,769 B1 | 4/2003 | Miller, III | |

(Continued)

*Primary Examiner* — Nicholas Woodall
*Assistant Examiner* — Melissa A Hall
(74) *Attorney, Agent, or Firm* — Stout, Uxa, Buyan & Mullins, LLP; Donald E. Stout

(57) ABSTRACT

A surgical tensioning device for dynamically holding two tissue portions in contact with one another comprises a resilient member having a plurality of extending portions which are spaced from one another and are capable of resiliently moving toward and away from one another. A plurality of attachment points are provided on the resilient member, for attaching a securing member, such as suture or a surgical screw, thereto. A spacer member is placeable between the plurality of extending portions to retain the extending portions at a fixed distance from one another, and is removable from between the plurality of extending portions after the securing members are in place so that said tension is transferred from the spring to the suture or other securing members. The result is an ability to hold two tissues in a state of compression beyond that which is commonly and consistently achieved with the hand tying of sutures.

13 Claims, 5 Drawing Sheets

U.S. PATENT DOCUMENTS

| | | |
|---|---|---|
| 6,547,725 B1 | 4/2003 | Paolitto et al. |
| 6,589,246 B1 | 7/2003 | Hack et al. |
| 6,648,903 B1 | 11/2003 | Pierson, III |
| 6,969,398 B2 | 11/2005 | Stevens et al. |
| 6,997,189 B2 | 2/2006 | Biggs et al. |
| 7,108,710 B2 | 9/2006 | Anderson |
| 7,341,558 B2 | 3/2008 | de la Torre et al. |
| 7,416,556 B2 | 8/2008 | Jackson |
| 7,722,632 B2 | 5/2010 | Rothstein et al. |
| 7,867,251 B2 | 1/2011 | Colleran et al. |
| 7,867,253 B2 | 1/2011 | McMichael et al. |
| 2002/0147449 A1* | 10/2002 | Yun .................................. 606/61 |
| 2003/0093117 A1 | 5/2003 | Saadat |
| 2005/0075653 A1 | 4/2005 | Saadat et al. |
| 2005/0090827 A1 | 4/2005 | Gedebou |
| 2005/0149121 A1 | 7/2005 | Crombie et al. |
| 2005/0240203 A1 | 10/2005 | Fuseri et al. |
| 2005/0251209 A1 | 11/2005 | Saadat et al. |
| 2007/0073289 A1 | 3/2007 | Kwak et al. |
| 2007/0112385 A1 | 5/2007 | Conlon |
| 2007/0213725 A1 | 9/2007 | Hack |
| 2007/0276437 A1 | 11/2007 | Call et al. |
| 2007/0293863 A1 | 12/2007 | Reimels et al. |
| 2007/0293864 A1 | 12/2007 | Reimels et al. |
| 2008/0004624 A1 | 1/2008 | Olroyd |
| 2008/0015589 A1 | 1/2008 | Hack |
| 2009/0062853 A1 | 3/2009 | McMichael et al. |

* cited by examiner

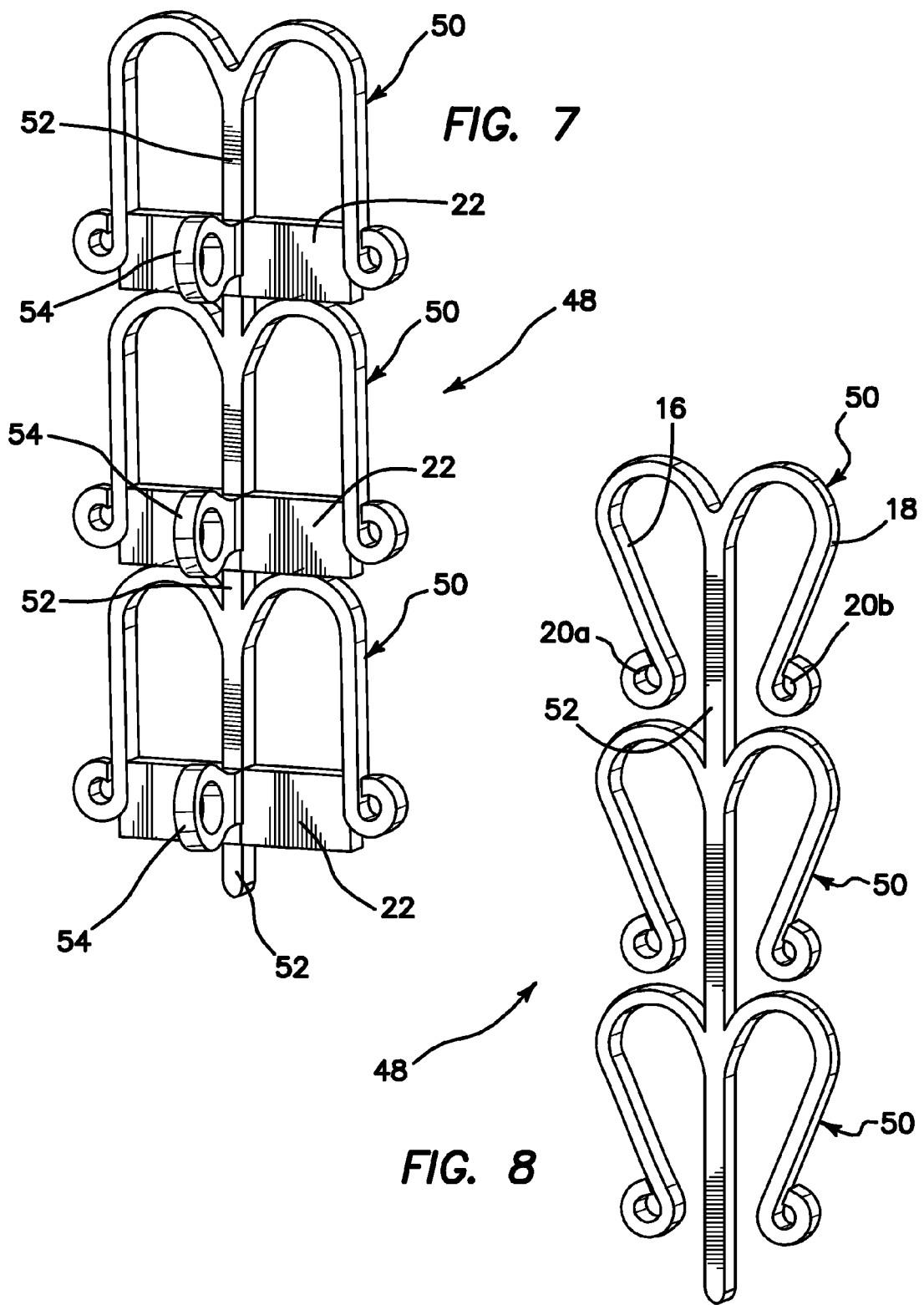

DYNAMIC SUTURE TENSIONING DEVICE AND METHODS

This application claims the benefit under 35 U.S.C. 119(e) of the filing date of Provisional U.S. Application Ser. No. 61/018,116, entitled Dynamic Suture Tensioning Device, filed on Dec. 31, 2007, and expressly incorporated herein by reference, in its entirety.

BACKGROUND OF THE INVENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote healing. Compression and stability are critical for proper anatomical healing of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

A common problem in using suture is the variable nature of the residual tension realized after the knot is tied. Hand tied knots usually supply only a fraction of the residual tension for which the suture is capable. There are various procedures where the residual tension in a hand tied knot is insufficient to approximate and generate the compression needed for healing between tissues.

There are times when high tension may cause suture to cut into tissue at points of stress concentration. This suture cutting may not happen immediately. It can take place as the tissue degrades or relaxes, or sometimes there are external forces that cause the suture to cut into the tissue. This cutting action releases tension in the suture and adversely affects the quality and durability of the repair.

What is needed, therefore, are devices and techniques for holding two tissue portions in a state of compression and tension beyond that which is commonly achieved using hand-tied sutures.

SUMMARY OF THE INVENTION

The present invention solves the problems outlined above by providing a means to approximate two tissue portions together so that there is compression in the tissue interface. The invention provides a means to hold two tissues in a state of compression beyond that which is commonly achieved with the hand tying of sutures. The invention may also be used to lengthen retracted tendons or ligaments. This is done by anchoring one end of the suture on bone and the other end on tendon or a ligament. The dynamic tensioning element in the invention serves to stretch and optionally attach the tendon or ligament to the bone. The spring may have many attachment and reattachment points for multiple lengths of suture. In such a configuration, the suture routes out into tissue and back to a reattachment point on the spring.

The tissue portions comprise biological tissue in the body, including, but not limited to, skin, tendon, bone, ligaments, blood vessels, and organs. The suture may comprise woven, braided, or knitted fibers or metals, or a monofilament, and can be made of any known suture material. The suture may be of any shape, including, but not limited to, round, square, oval, flat (like a strap), or tubular. This invention provides in certain embodiments a suture that can supply desired residual tension and elasticity after the knot is tied. The invention also provides the ability to hand tie a knot and get residual tension which approaches the tensile performance of the suture.

The invention in many embodiments consists of a length of suture and a tensioned spring. The tensioned spring is tensioned such that it is easily released. The suture is attached to the spring and generally to a needle on the other end. The suture is woven or stitched into tissue such that the needle end of the suture is brought back to the spring. The needle end is now attached to the spring with either a knot or by means of or in conjunction with a mechanism. The properties of the suture-spring construct are determined by a person's variable ability to attach the suture to the spring. The spring is then released. In being released, the spring now overrides and determines the properties of the suture-spring construct. The desired tension and the elasticity are engineered into the spring to provide consistent desired properties in the construct.

This invention may be used in conjunction with other devices that anchor into or onto bone or tissue.

Reattachment points on the spring may have a post or an eyelet to facilitate knot tying. Reattachment points may also have cleats or buckles that may be used alone or in conjunction with a knot. Reattachment points may also have mechanisms that provide for secure attachment without the use of a knot.

The suture may be defined by that which is normally available. It may be woven fibers or a monofilament and can be any material. On one end of the suture may be a needle or other receptacle to facilitate stitching or weaving in tissue or bone. Alternatively, there may be attached a receptacle to facilitate the mating of a tissue or bone anchor. Alternatively, there may be attached a receptacle to facilitate the mating or attachment of an implant. The other end of the suture is attached to the spring.

The spring can be made of any material and of any configuration as long as it has a smaller spring constant than that of the suture. The spring may be a flat spring, wound spring, elastic spring, or torsion spring.

There are provisions on the spring for attachment of the other end of the suture. This may merely be a loop or could be a post or eyelet. Alternatively there may be provided a cleat or buckle to facilitate a tight attachment of the suture. Such a cleat or buckle may require that the suture still be knotted. Alternatively, there may be a mechanism that provides for the knotless attachment of the suture.

There are provisions within the system to have the spring in its fully tensioned/extended state while the other end/s of the suture is/are being attached. Extension of the spring may be done manually by the user or may be provided for by the manufacturer prior to packaging. Extension is held while attaching the other end of the suture and then released. Holding and releasing the extension of the spring may be done manually with an instrument such as a hemostat. Extension may also be maintained by a spacer that is removable. Extension may also be maintained by a mechanism that creates and releases the extension.

There may be one or more sutures attached to the spring. For every suture that is attached to the spring, there is a site on the other side of the spring for the suture to be attached.

More particularly, there is provided a surgical tensioning device for dynamically holding two tissue portions in contact with one another. This device comprises a resilient member having a plurality of extending portions which are spaced from one another and are capable of resiliently moving toward and away from one another. A plurality of attachment points on the resilient member are provided, for attaching a securing member thereto. A spacer member is placeable between the plurality of extending portions to retain the extending portions at a fixed distance from one another, and is removable from between the plurality of extending portions so that the extending portions are free to flex toward and away from one another.

In certain preferred embodiments, one of the plurality of attachment points is disposed on a distal end of one of the extending portions, and another of the plurality of attachment points is disposed on a distal end of another of the extending portions. In some embodiments a securing member re-attachment post is provided on the resilient member.

The resilient member preferably comprises a spring having a base portion, wherein the plurality of extending portions comprise legs spaced from one another and upstanding from the base portion. The legs each have distal ends, and one of the plurality of attachment points is disposed on each of the leg distal ends. The suture attachment points may comprise a loop or hook.

The securing member preferably comprises a length of suture for attaching to the resilient member, wherein one end of the suture comprises a member for facilitating entry of the one end into desired tissue. The facilitating member preferably comprises a needle, and is removable from the suture when a surgical procedure using the suture is completed. In alternative embodiments, typically involving rigid tissue such as bone, the securing member may comprise a screw for insertion into the rigid tissue.

In some embodiments, the inventive device may further comprise a second resilient member which is attached to the resilient member. The second resilient member also comprises a plurality of extending portions which are spaced from one another and are capable of resiliently moving toward and away from one another. A support element, in some embodiments, which may comprise a post, extends from the resilient member to the second resilient member, and connects the two resilient members to one another.

In another aspect of the invention, there is disclosed a method for securing together two spaced bodily tissues with a surgical tensioning device, which comprises a resilient member having first and second extending portions spaced from one another and capable of resiliently moving toward and away from one another. This inventive method comprises a step of placing the resilient member so that it straddles an opening separating two portions of bodily tissue to be joined, with the first extending portion disposed on or in proximity to tissue on one side of the opening and the second extending portion disposed on or in proximity to tissue on a second side of the opening. A first securing member is attached to an attachment point on the first extending portion, and a second securing member is attached to an attachment point on the second extending portion. The placing step preferably includes a step of ensuring that a spacer member is disposed between the two extending portions to maintain the extending portions at a substantially fixed distance from one another, and to take up excess tension in the resilient member. A step of releasing tension in the resilient member after the second securing member is attached to the attachment point on the second extending portion is then performed. The releasing step is performed by removing the spacer member.

In some cases, the bodily tissue comprises bone, and the first and second securing members comprise screws. In other cases, the bodily tissue comprises soft tissue, the first securing member comprises a first end of a length of suture, and the second securing member comprises a second end of the length of suture.

The inventive method may further comprise a step of passing the second end of the length of suture through the soft tissue between the two attaching steps.

The invention, together with additional features and advantages thereof, may best be understood by reference to the following description taken in conjunction with the accompanying illustrative drawings.

BRIEF DESCRIPTION OF THE DRAWINGS

FIG. 7 is a view similar to FIG. 1, illustrating a third embodiment of the device of the present invention, employing three springs;

FIG. 8 is a view similar to FIG. 7, showing the springs with their spacers removed.

DESCRIPTION OF THE PREFERRED EMBODIMENT

Figure 1:
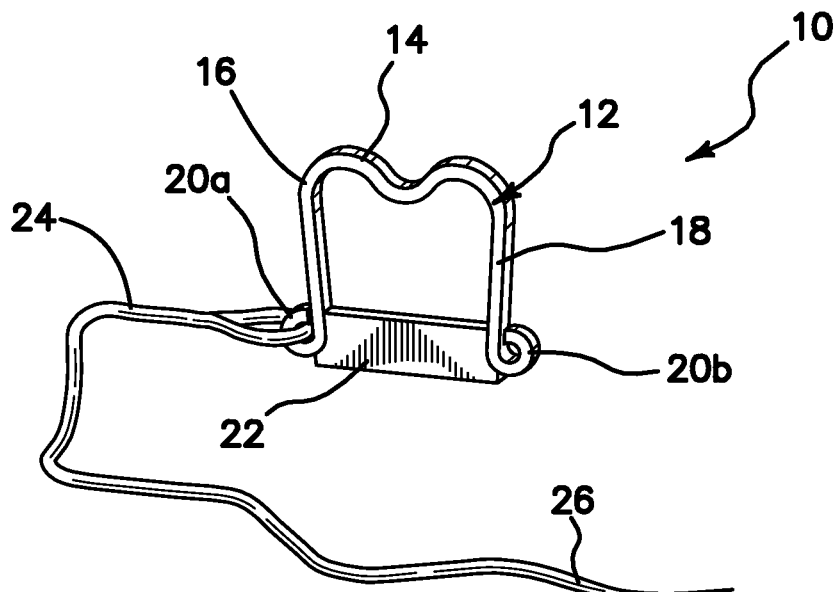
FIG. 1 is a plan view illustrating a first embodiment of the device of the present invention.
Figure 2:
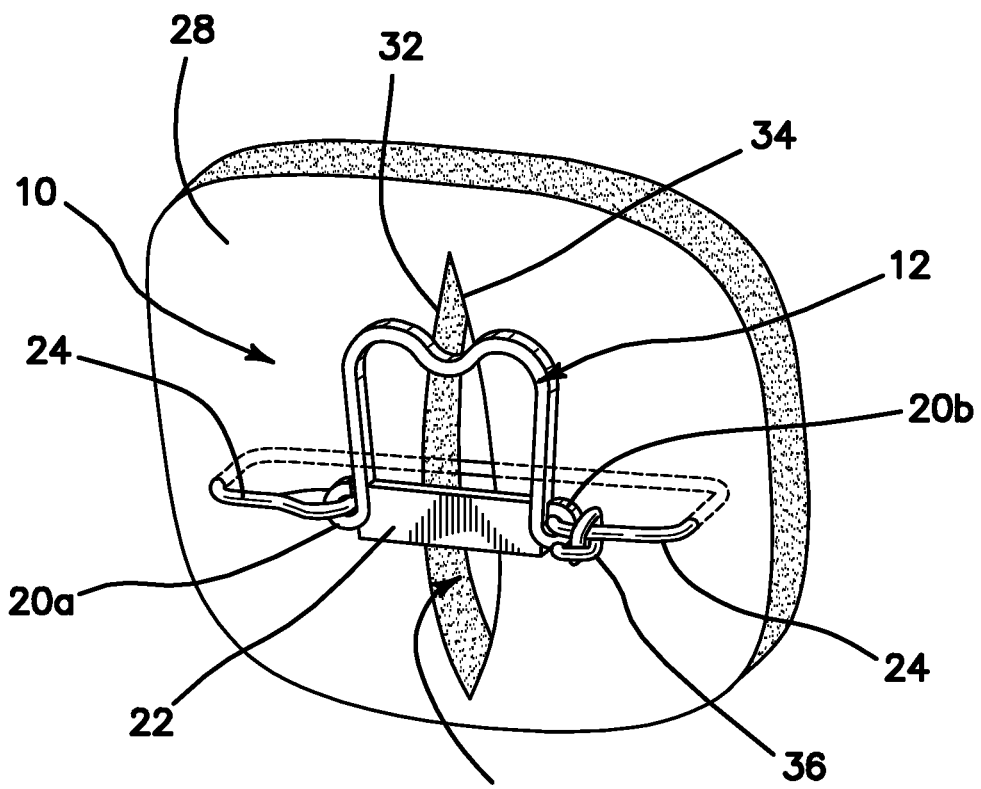
FIG. 2 is a view similar to FIG. 1, illustrating the embodiment of FIG. 1 in position for approximating two tissue portions together at the site of a lesion.
Figure 3:
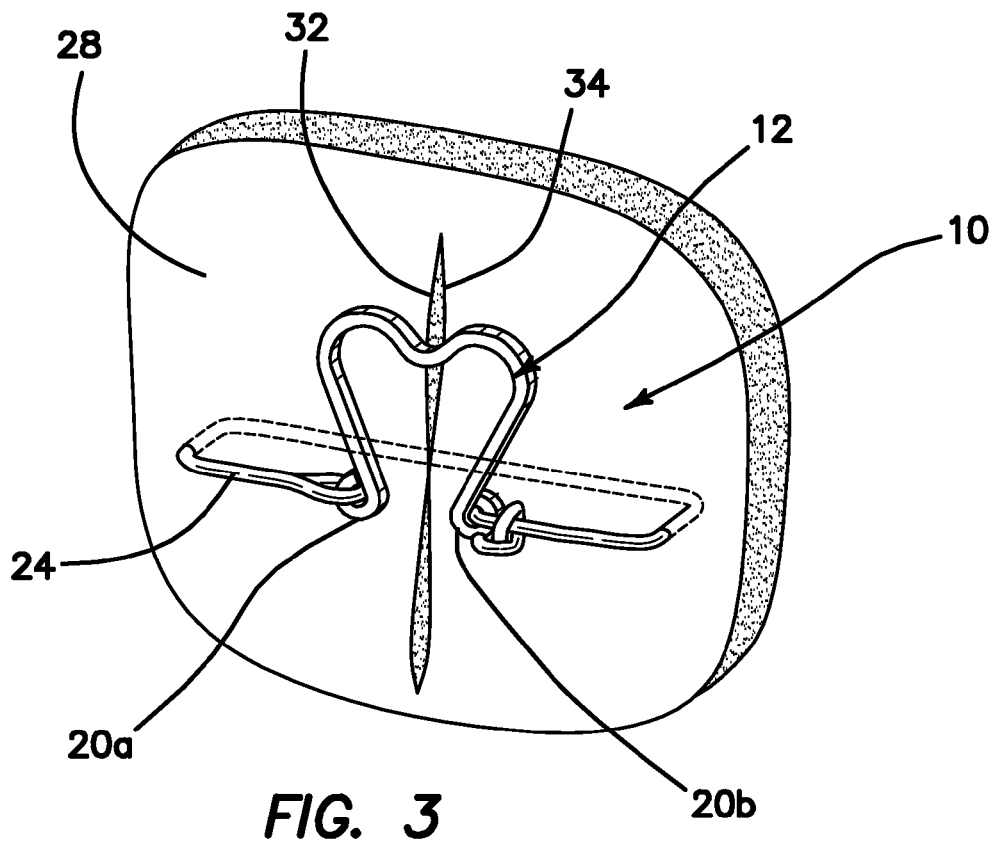
FIG. 3 is a view similar to FIG. 2, illustrating the tissue portions after they have been approximated by the inventive device.

Referring now more particularly to the drawings, there is shown in FIGS. 1-3 a "single suture" embodiment 10 of the present invention. The device 10 comprises a resilient member or spring 12 which is generally shaped like the letter "U", with a base portion 14 and upstanding legs 16, 18. Each upstanding leg includes, at its end distal to the base portion 14, an attachment point 20a, b, respectively, each of which may comprise a loop or hook, as shown, or other suitable configurations. A spacer member 22, comprised of a suitable length of rigid biocompatible material, is disposed between the respective distal ends of each upstanding leg 16, 18 to hold the spring 12 in a tensioned state. The spring 12 is comprised of a suitable resilient biocompatible material.

A length of suture 24 is attached to attachment point 20a at one end thereof, as shown, to thereby attach the suture to the spring 12. The suture 24 is to be woven or stitched with the aid of a needle 26.

FIG. 2 illustrates the device 10 of FIG. 1 as it may be situated on a portion of representative tissue 28 in the vicinity of a lesion 30 having respective sides 32 and 34 that are in need of approximation. The suture 24 is routed with the needle 26 from its attachment point 20a through tissue side 32 around the back side of the lesion 30 to and through the other tissue side 34 to its other attachment point 20b. At this juncture, the needle 26 is removed, the suture 4 is tensioned to a desired level, and a knot 36 is tied at and about the attachment point 20*b*, as shown. Once this securing step has been completed, the spacer 22 is removed from the spring 12, to transfer any tension on the spacer 22 to the suture 24.

FIG. 3 shows the device 10 of the present invention with the spacer 22 removed. As can be seen, the two sides 32, 34 of the tissue 28 is now further approximated by the transference of tension from the spacer 22 to the suture 24. Because the spacer 22 was holding a known tension in the spring 12, prior to its removal, the tension now residing in the suture 24 is known as well. Furthermore, the tension set in the spring can approximate the tensile strength of the suture if desired. Such a tension is difficult to achieve and to regulate, if relying solely on hand tied knots, rather than the spring device 10 of the present invention. Thus, the inventive system and methods assists substantially in allowing for the effective management of compression in the repair. This effectively puts the tissue in a state of compression, which is commonly desired to promote healing.

This state of compression is dynamic in that external forces may cause tissue sides 32 and 34 to separate. In the event of such an occurrence, the inventive spring arrangement of the present invention will cause the spring 12 to extend with the applied external forces, and then to retract, due to the potential energy of the spring, to re-establish the desired compression. Without this dynamic compression, the sutures would likely cut into the tissue 28 upon application of the above noted external forces, thus causing compression on the lesion, important to the repair process, to be permanently lost.

Figure 4:
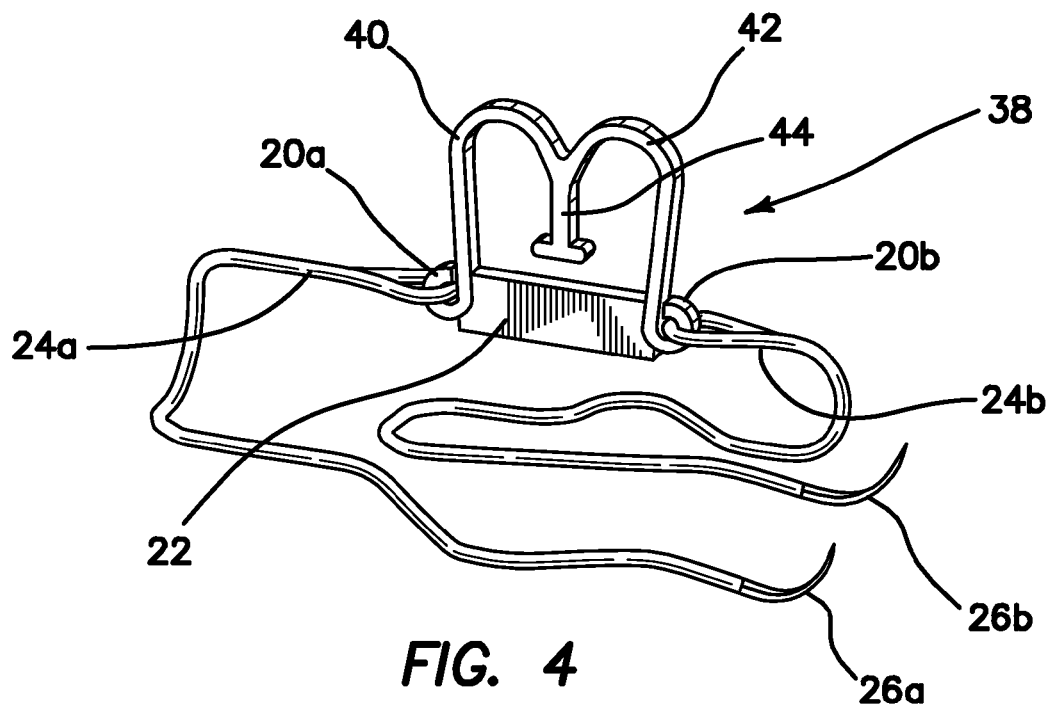
FIG. 4 is a view similar to FIG. 1, illustrating a second embodiment of the device of the present invention having two sutures.
Figure 5:
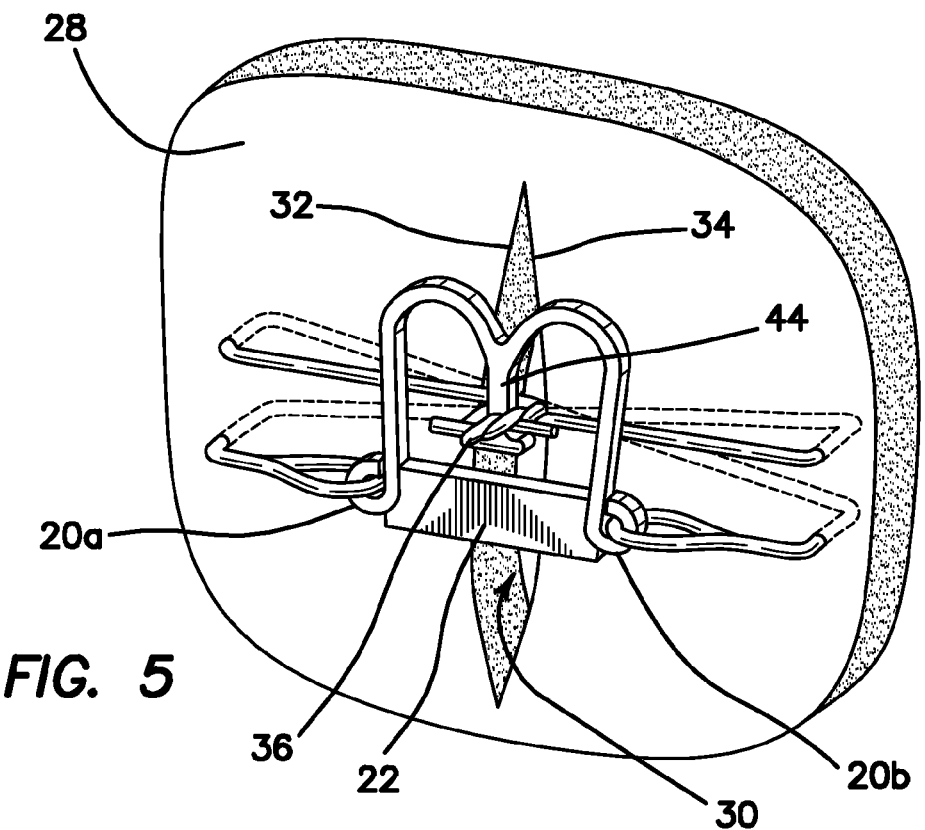
FIG. 5 is a view similar to FIG. 4, illustrating the embodiment of FIG. 4 in position for approximating two tissue portions together at the site of a lesion.
Figure 6:
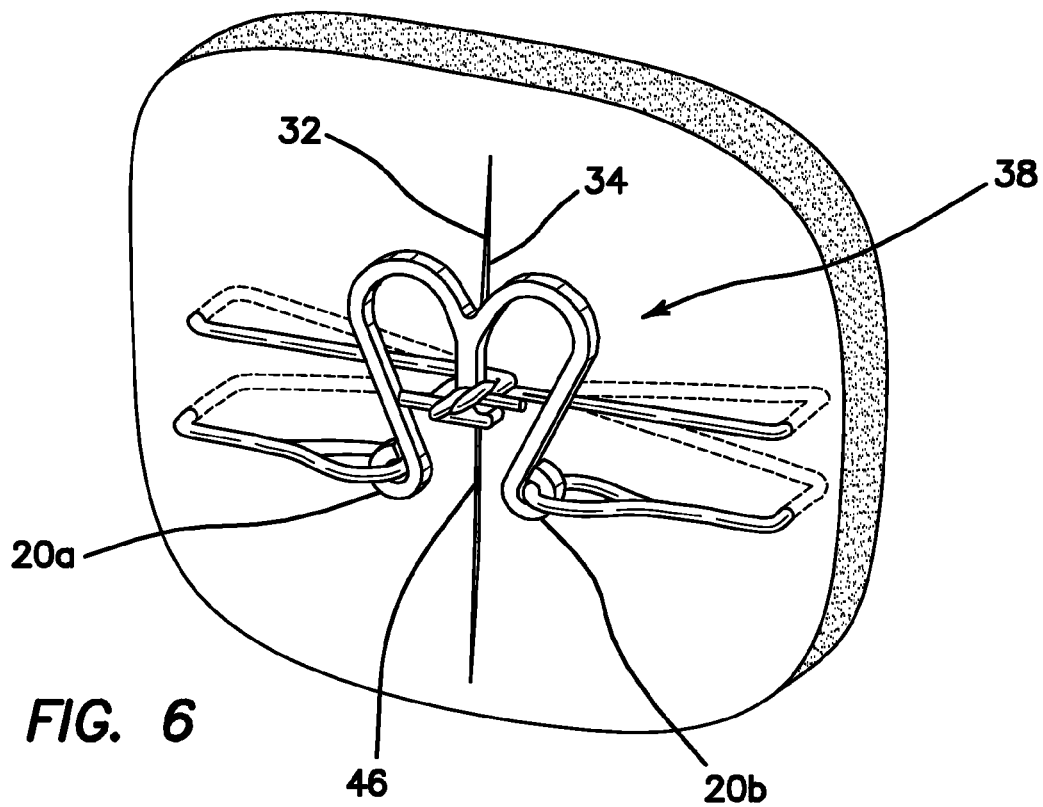
FIG. 6 is a view similar to FIG. 5, illustrating the tissue portions after they have been approximated by the inventive device.

FIGS. 4-6 illustrate a modified embodiment of the invention, wherein two different lengths of suture 24*a* and 24*b* are employed. It is noted that like elements to those illustrated in the embodiment of FIGS. 1-3 are identified by like reference numerals. Thus, in FIG. 4, there is shown a double suture embodiment 38 comprising two springs 40 and 42, respectively. Suture length 24*a*, having a needle 26*a* disposed at the distal end thereof, is attached to attachment point 20*a* on the spring 40, while the second suture length 24*b*, having a needle 26*b* disposed on its distal end, is attached to the attachment point 20*b* on the spring 42. As in the prior embodiment, the purpose of the needles 26*a* and 26*b* is to facilitate placement in tissue. A single spacer 22 is used in this embodiment, as illustrated. However, in alternative approaches, two such spacers may be advantageous, one for each of the springs 40 and 42. A single suture re-attachment point 44 is employed in this embodiment, preferably in the form of a post, as illustrated. Separate re-attachment points may be desirable in other embodiments, that may employ cleats or other mechanisms. Still other embodiments may have cinching mechanisms that require only one re-attachment site for multiple sutures. In such an alternative embodiment, the attachment and re-attachment points may be reversed due to the complexity of the mechanism, and the looped end of the suture may be attached to the needle, which subsequently gets detached from the needle and attached to the springs at attachment points 20*a*, 20*b*, respectively.

FIG. 5 illustrates the embodiment 38, as it is disposed on a tissue portion 28 in accordance with the principles of the present invention. As shown in FIGS. 2 and 3, the tissue 28 has a lesion 30 that has sides 32 and 34 that are in need of approximation. The suture 24*a* is routed, using its needle 26*a*, from its attachment point 20*a* through the tissue side 32, crossing the lesion 30, then back through the opposing tissue side 34 and onto the re-attachment point or post 44. Similarly, the suture 24*b* is routed, using its needle 26*b*, from its attachment point 20*b*, through the tissue side 34, crossing the lesion 30, then back though the opposing tissue side 32 and also onto the re-attachment point or post 44. The needles 26*a*, 26*b*, respectively, are then removed, the sutures 24*a*, 24*b* are routed around the back of the post 44, and tensioned to a desired level, after which a knot 36 is tied on top of the post 44, as illustrated. Following this step, the spacer 22 is removed in order to transfer the tension from the spacer 22 to the sutures 24*a*, 24*b*.

FIG. 6 illustrates the device 38 with the spacer 22 removed. As can be seen, the tissue sides 32 and 34 are now further approximated to a point where the lesion is substantially closed, by the transference of tension from the spacer to the suture. The suture attachment points 20*a* and 20*b* have moved closer together to move the tissue closer together at a tissue interface 46. This embodiment has the same preferred dynamic tissue compression as the prior embodiment illustrated in FIGS. 1-3, as well as suture tensioning properties. This demonstrates how the inventive concept may use a single component to dynamically tension multiple sutures.

Figure 9:
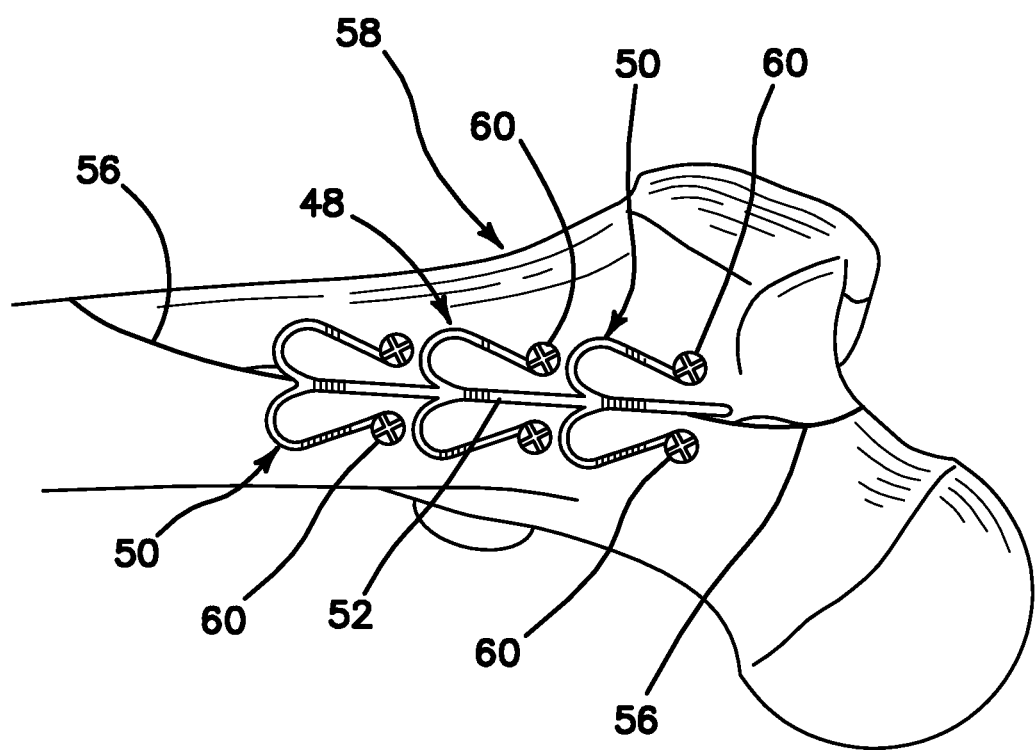
FIG. 9 is a view illustrating the embodiment of FIGS. 7 and 8 deployed along a fracture line in a patient's femur.

In FIGS. 7-9 there is shown yet a third representative embodiment 48 of the present invention. In this embodiment 48, a plurality of springs 50 are fixed to one another, as shown. The springs 50 are bridged together by means of a support shaft or element 52. This support element 52 may be either rigid or malleable, or may have spring properties similar to those of the springs 50. Each spring set 50 includes its own spacer 22. Each spacer 22 includes an eyelet member 54 which is adapted to serve as a site to purchase the spacer with an instrument such as a hook. Other gripping features that interface with common surgical instruments may be incorporated in alternative embodiments. Each spacer 22 is trapped in its respective spring 50 by means of forces imparted by springs 50 at attachment points 20*a* and 20*b*, respectively. The spacer may also be supported in place by adjoining spring members 50 and the support element 52. Suture may be attached at the attachment point 20*a*, for example, and routed through tissue to be reattached to the spring 50 at the attachment point 20*b* (equally, the suture could first be attached to attachment point 20*b*, and re-attached at attachment point 20*a*. In alternative embodiments, screws may be used to attach each spring 50, at attachment points 20*a*, 20*b*, to bony tissue.

In FIG. 8, the embodiment 48 of FIG. 7 is illustrated with the spacers 22 removed from each spring set 50. The legs 16, 18 of each spring 50 articulate together as a result of removal of the spacer 22. In practice, the support element 52 is manipulated to be lined up along the tissue edges as needed for approximation.

FIG. 9 illustrates a representative application for the embodiment 48 of FIGS. 7 and 8. As shown, the support element 52 is lined up along a fracture line 56 in a femur 58 of a patient. The illustrated embodiment shows three spring sets 50 disposed along the fracture line 56. However, more spring sets may be preferred to hold these bony tissues together, depending upon the length of the fracture. Screws 60 are utilized to attach each spring set 50 to adjacent bony tissue. Often, there is an intramedullary implant that prevents the effective usage of screws. Should such an implant be present, cerclage sutures may be used instead of or supplemental to some or all of the screws 60, attached at the same points 20*a*, 20*b* on each screw.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A surgical tensioning device for dynamically holding two tissue portions in contact with one another, the device comprising:
   a first resilient member having a plurality of extending portions which are spaced from one another and are capable of resiliently moving toward and away from one another;
   a plurality of attachment points on said first resilient member, for attaching a securing member thereto;
   a spacer member which is placeable between said plurality of extending portions to retain said extending portions at a fixed distance from one another, and is removable from between said plurality of extending portions so that said extending portions are free to flex toward and away from one another; and
   a second resilient member which is attached to said first resilient member, said second resilient member also comprising a plurality of extending portions which are spaced from one another and are capable of resiliently moving toward and away from one another.

2. The surgical tensioning device as recited in claim 1, wherein one of said plurality of attachment points is disposed on a distal end of one of said first resilient member extending portions, and another of said plurality of attachment points is disposed on a distal end of another of said first resilient member extending portions.

3. The surgical tensioning device as recited in claim 2, and further comprising a securing member re-attachment post on said first resilient member.

4. The surgical tensioning device as recited in claim 1, wherein said first resilient member comprises a spring having a base portion, said plurality of extending portions comprising legs spaced from one another and upstanding from said base portion.

5. The surgical tensioning device as recited in claim 4, wherein said legs each have distal ends, and one of said plurality of attachment points is disposed on each of said leg distal ends.

6. The surgical tensioning device as recited in claim 1, wherein said suture attachment points comprise a loop or hook.

7. The surgical tensioning device as recited in claim 1, and further comprising a securing member which comprises a length of suture for attaching to said first resilient member, wherein one end of said suture comprises a member for facilitating entry of said one end into desired tissue.

8. The surgical tensioning device as recited in claim 7, wherein said facilitating member comprises a needle.

9. The surgical tensioning device as recited in claim 7, wherein said facilitating member is removable from the suture when a surgical procedure using the suture is completed.

10. The surgical tensioning device as recited in claim 1, wherein said securing member comprises a screw for insertion into rigid tissue, such as bone.

11. The surgical tensioning device as recited in claim 1, and further comprising a support element extending from said first resilient member to said second resilient member, and connecting said first and second resilient members to one another.

12. The surgical tensioning device as recited in claim 11, wherein said support element comprises a post.

13. The surgical tensioning device as recited in claim 1, wherein said spacer member comprises a body having opposing ends, and further wherein when said spacer member is placed between said plurality of first resilient member extending portions, a first end of said body contacts one of said plurality of first resilient member extending portions and a second end of said body contacts another one of said plurality of first resilient member extending portions to hold the plurality of first resilient member extending portions a fixed distance apart.

* * * * *